United States Patent [19]

Tucker

[11] Patent Number: 4,605,403
[45] Date of Patent: Aug. 12, 1986

[54] SANITARY NAPKIN DISPOSAL SYSTEM

[75] Inventor: J. Camille Tucker, San Antonio, Tex.

[73] Assignee: Dalal Hibril, San Antonio, Tex.

[21] Appl. No.: 720,698

[22] Filed: Apr. 8, 1985

[51] Int. Cl.[4] ............................................. A61F 13/16
[52] U.S. Cl. ................................................. 604/385 R
[58] Field of Search .............. 604/385, 386, 387, 358, 604/401; 206/438

[56] References Cited

U.S. PATENT DOCUMENTS 3,274,999  9/1966  Robinson ............................ 604/385
4,182,336  1/1980  Black .................................. 604/385

Primary Examiner—John D. Yasko
Attorney, Agent, or Firm—Gunn, Lee & Jackson

[57] ABSTRACT

A method and apparatus for effecting the sanitary disposal of soiled sanitary napkins comprises the fabrication of a disposal bag from a flexible plastic or paper sheet material on conventional bag forming machines. The bag thus formed is incorporated in the structure of the pad, either by adhesively securing the bag to an inactive face of the pad or inserting the folded bag between a liquid impermeable plastic sheet incorporated in the sanitary napkin and a surrounding gauze cover. When disposed of the soiled napkin is desired, the folded bag may be quickly and conveniently removed from the soiled napkin and the soiled napkin deposited therein for disposal.

11 Claims, 9 Drawing Figures

SANITARY NAPKIN DISPOSAL SYSTEM

BACKGROUND OF THE INVENTION

1. Field of the Invention

The invention relates to a sanitary napkin and particularly to a method and apparatus permitting the convenient disposal of a used napkin.

2. Summary of the Prior Art

A sanitary napkin is periodically worn by practically every female. In recent years, sanitary napkins have been designed with adhesive strips on one side thereof to permit the napkin to be conveniently adhered to the inside of a tight fitting undergarment, such as panties or panty hose. While the comfort and securement of sanitary napkins has been improved, there has not been a corresponding improvement in the ease of disposal of such napkins. It has been proposed, for example, in U.S. Pat. No. 3,035,578 to Elmore that a disposable cover be folded and adhesively secured to the non-active side of the sanitary napkin whereupon a used napkin may be wrapped in the cover which is stripped from its adhesive securement to the napkin. This involves an unnecessary amount of activity for the napkin user and also does not insure that the wrapping around the soiled napkin will remain in place. See also U.S. Pat. No. 3,973,567 to Srinivasan, et al.

Other prior patents, such as U.S. Pat. No. 3,024,788 to Lane, U.S. Pat. No. 3,230,956 to Kargul, U.S. Pat. No. 3,274,999 to Robinson, U.S. Pat. No. 3,604,423 to Fraser, and U.S. Pat. No. 4,182,336 to Black, have proposed that various configurations of envelopes be fabricated as an integral part of the sanitary napkin, and generally reversely folded to encompass the soiled napkin. These constructions are characterized by high cost of manufacture, since the fabrication of an envelope as an integral part of a sanitary napkin is inherently costly. The prior art has not really solved the problem of providing an economical method and apparatus for effecting the sanitary disposal of soiled sanitary napkins.

SUMMARY OF THE INVENTION

This invention provides a method and apparatus for sanitary disposition of soiled sanitary napkins comprising the utilization of a simple, economically fabricated plastic bag which is removably incorporated in the napkin construction. In one embodiment of the invention, the plastic bag may be folded to a configuration less in area than the area of the sanitary napkin and inserted in a slit cut in an encompassing perforated gauze that normally surrounds the absorbent materials of the plastic napkin. The bag lies on the outer face of a liquid impermeable packing layer which is conventionally provided on a sanitary napkin and under the surrounding gauze, thus avoiding any soiling of the folded disposal bag.

In another embodiment of the invention, the conventionally manufactured plastic bag is folded to a configuration having a smaller area than that of the sanitary napkin and is adhesively secured to the inactive or outer face of the sanitary napkin which is normally adhesively secured to a close fitting undergarment of the user. In this modification, the folded plastic bag is provided with adhesive bands on the both of its outer surfaces with the one set of bands adhesively engaging the napkin and the outer set of bands adhesively engaging the tight fitting undergarment of the user. Hence, the bag acts as a means for securing the sanitary napkin to the undergarment of the user.

In both modifications of the invention, the bag is fabricated entirely separate from the sanitary napkin and hence can fully utilize the high productivity inexpensive machines now in existence in the paper bag industry and the plastic film industry for forming plastic bags. Since the mounting of the economically formed plastic or paper bag upon or in the sanitary napkin involves a very simple operation, the total manufacturing costs of the napkin and its disposal container is significantly reduced. Moreover, the sanitary napkin disposal system embodying this invention has the decided advantage of not requiring the user to store a plastic bag in a purse in anticipation of using the bag when the sanitary napkin being worn becomes soiled.

Further objects and advantages of the invention will be readily apparent to those skilled in the art from the following detailed description, taken in conjunction with the annexed sheets of drawings on which are shown several preferred embodiments of the invention.

DESCRIPTION OF THE PREFERRED EMBODIMENTS

Figure 1:
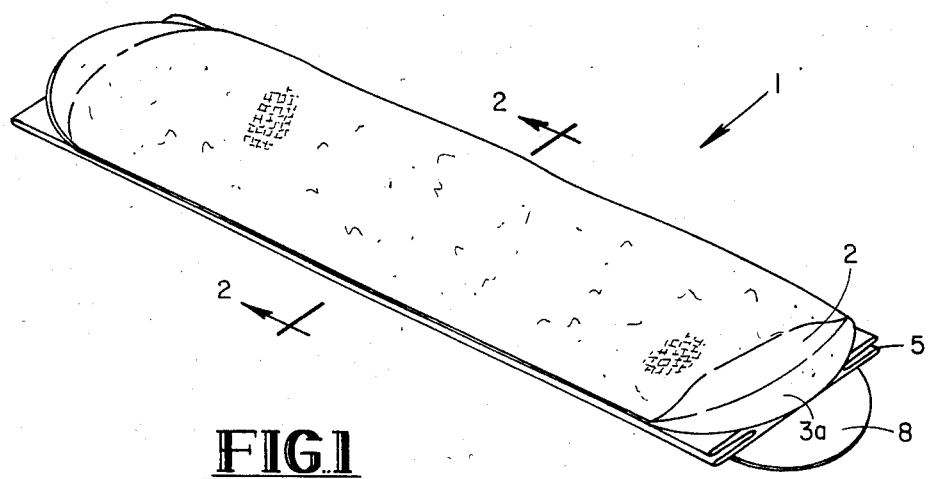
FIG. 1 is a perspective view of a sanitary napkin and disposal bag shown in assembled relationship ready for application to the undergarment of a user.
Figure 2:
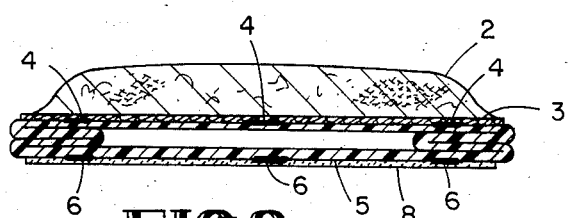
FIG. 2 is an enlarged scale cross-sectional view taken on the plane 2—2 of FIG. 1.
Figure 3:
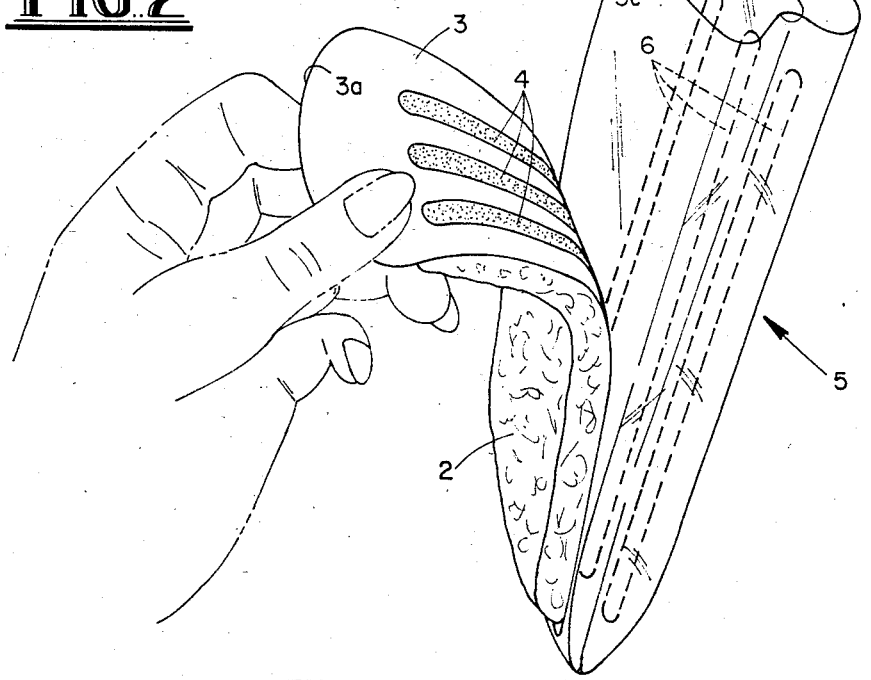
FIG. 3 is a schematic perspective view illustrating the method of separating the plastic bag from the soiled napkin.

Referring to FIGS. 1-3 and particularly to FIG. 2, there is shown a conventional sanitary napkin 1 comprising a pad of absorbent material 2 which has the one face of the pad bonded or suitably secured to a sheet 3 of impermeable plastic. The exposed face of the plastic sheet 3 is provided with bands of tacky or pressure sensitive adhesive 4 which would normally be employed to effect the mounting of the sanitary napkin to the inner portions of a tight fitting undergarment. A removable paper cover 8 protects adhesive bands 4 prior to usage of the napkin.

In accordance with this invention, a plastic or paper disposal bag 5 is fabricated on conventional high volume plastic or paper bag making machines and is then folded by bending two opposed sides 5a and 5b in reentrant fashion, as best shown in FIG. 3, so that the total area dimensions of the folded bag are somewhat less than the dimensions of the sanitary napkin 1. The bag 5 then has one of its unfolded walls 5c removably secured to the adhesive bands 4. The other wall 5d, which becomes the face of the napkin assemblage which will be adjacent the user's undergarment, is provided with one or more parallel bands of a tacky or pressure sensitive adhesive 6, and these bands of adhesive 6 are employed for mounting the assembled sanitary napkin 1 and disposal bag 5 to the inner surfaces of a tight fitting undergarment of the user. If desired, the absorbent portion 2 of the sanitary napkin 1 may be wapped in a permeable gauze-like material, but such wrapping is not herein shown for convenience of illustration. In any event, the construction of the sanitary napkin 1 is exactly the same as that employed in conventional napkins and the efficiency of its operation is in no manner impaired by the securement of the folded disposal bag 5 to the inactive surface of the napkin.

When the napkin 1 is soiled so that disposal is desired, the tab-like end 3a of the non-permeable plastic sheet material 3 may be engaged by the fingers and the plastic bag 5 can be readily stripped from the rest of the napkin 1 and the mouth thereof opened as indicated in FIG. 3 to permit the soiled napkin 1 to be conveniently inserted within the plastic or paper bag 5.

Figure 4:
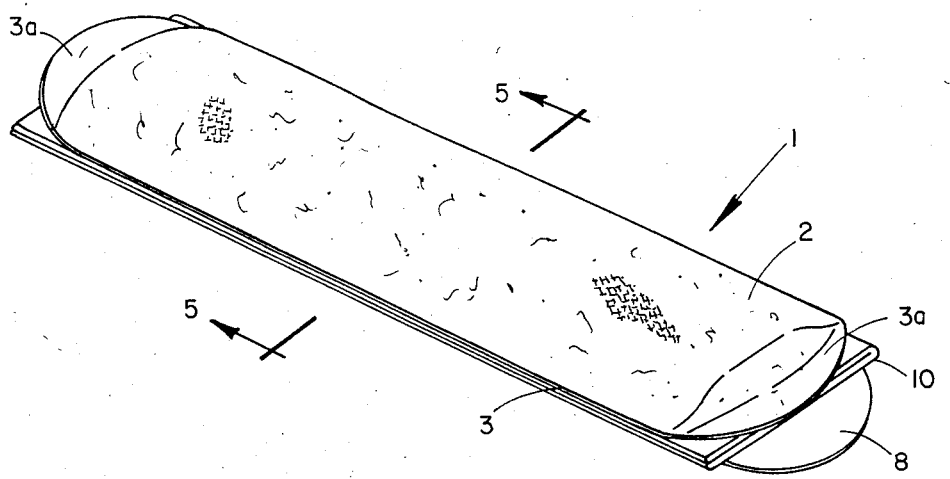
FIG. 4 is a perspective view of a modified form of sanitary disposal bag wherein the bag is of substantially greater width dimensions than the sanitary napkin.
Figure 5:
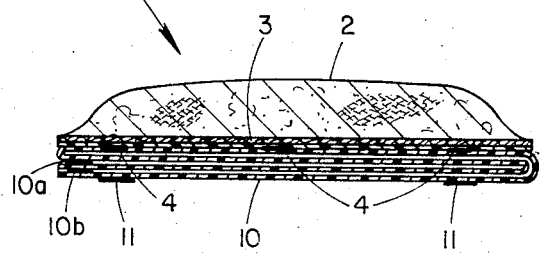
FIG. 5 is an enlarged scale sectional view taken on the plane 5—5 of FIG. 4.
Figure 6:
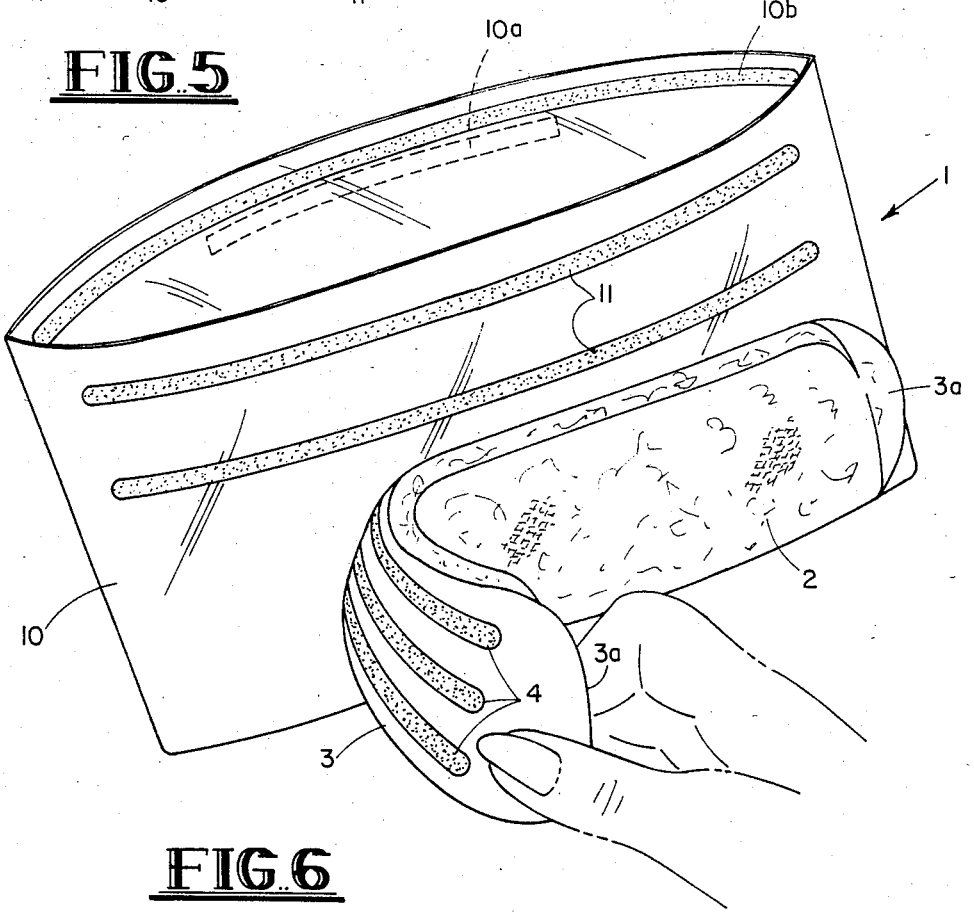
FIG. 6 is a schematic perspective view illustrating the removal of the disposal bag from the soiled sanitary napkin.

In the modification of FIGS. 4 through 6, the same principles are utilized as described in connection with the previous modification, but the overall dimensions, and particularly the lateral dimensions of the disposal bag 10, are substantially larger. As best shown in FIG. 6, the disposal bag 10 comprises a conventionally fabricated plastic bag having a height dimension almost double that of the width of the sanitary napkin 1 and a length dimension approximately equal to the napkin 1, as seen in FIGS. 4 and 6. The disposal bag 10 is adhered to the bands of adhesive 4 employed on the back surface of the liquid impermeable sheet of plastic 3 and the bag 10 is thereby secured to such surface.

The bag 10 is then folded longitudinally and an adhesive strip 10a provided on the back surface of the bag 10 secures the folded bag in its folded position illustrated in FIGS. 4 and 5 by engagement with the adjacent surface of the bag 10.

Two or more longitudinally extending bands of adhesive 11 are provided on that portion of the surface of bag 10 which is not covered by the impermeable plastic backing 3 of the sanitary napkin 1. When bag 10 is longitudinally folded, these strips of adhesive 11 provide the means for effecting the securement of the completely assembled sanitary napkin 1 and bag 10 to the inside surfaces of the undergarment of the user. An adhesive band 10a secures the bag 10 in its folded configuration. A paper cover 8 protects the adhesive strips 11 prior to use.

When the napkin 1 is soiled, it is only necessary to unfold the bag 10 to its original configuration illustrated in FIG. 6 and thereupon a very large disposable pouch is provided for receiving the soiled sanitary napkin 1 which can be stripped by the fingers of the user from its adhesive engagement with the side wall of the open bag 10. Once the soiled napkin is inserted in the bag 10, the bag 10 can be refolded and adhesively secured by a band 10b in such longitudinally folded condition, thereby completely sealing the soiled napkin within the confines of the unfolded bag 10.

Figure 7:
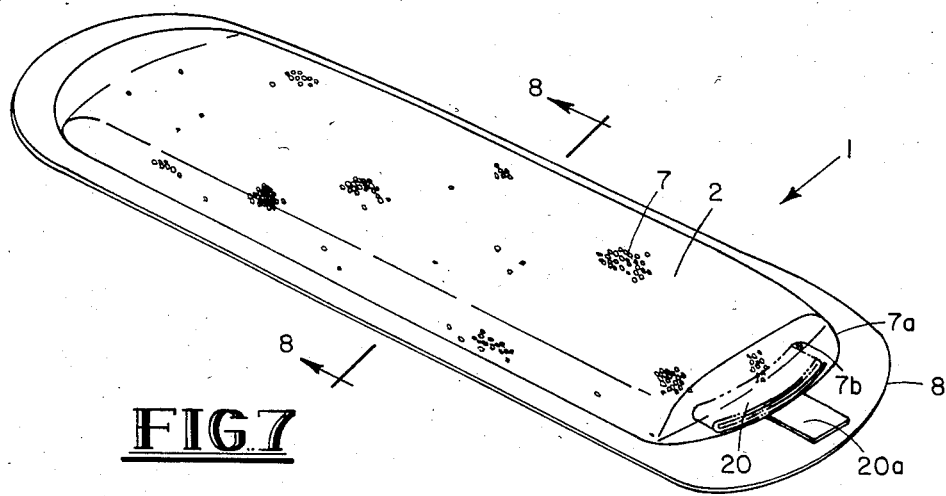
FIG. 7 is a perspective view of still another embodiment of a sanitary napkin and disposal bag embodying this invention.
Figure 8:
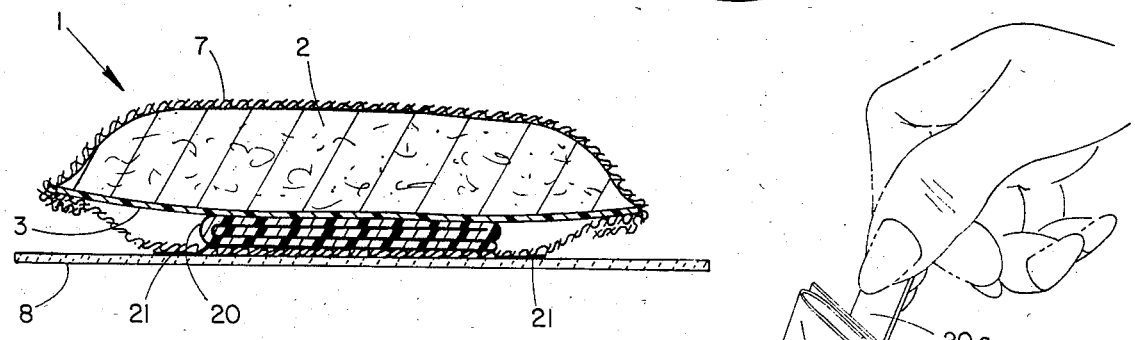
FIG. 8 is an enlarged scale sectional view taken on the plane 8—8 of FIG. 7.
Figure 9:
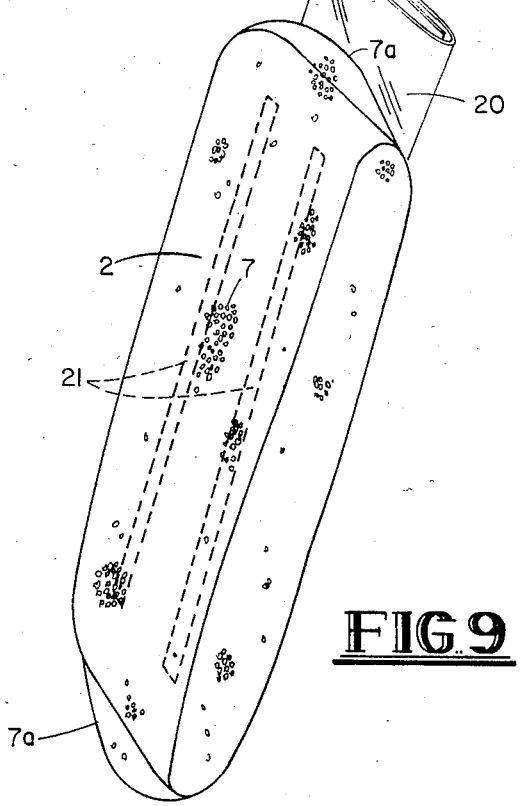
FIG. 9 is a schematic perspective view illustrating the removal of the folded plastic bag from the interior of a soiled sanitary napkin.

A preferred embodiment of this invention is illustrated in FIGS. 7 through 9 wherein the same reference numerals indicate components similar to those already described. Thus, the sanitary napkin 1 is here shown as a pad of absorbent material 2 which has one face thereof suitably secured to a liquid impermeable sheet of plastic 3. Both the absorbent material 2 and the plastic sheet 3 are then encased in a soft, flexible, perforated, gauze-like material 7, the ends of which may be adhesively secured together as indicated at 7a. A slit 7b is provided, extending transversely across one end of the gauze material below the adhesively secured ends 7a. Slit 7b extends for a distance of less than the full width of the napkin, as seen in FIG. 7. The plastic disposal bag 20 is now folded into a configuration substantially smaller in width dimension that the dimensions of the pad and such bag may be conveniently inserted through the slit 7b to lie intermediate the gauze 7 and the impermeable plastic sheet 3.

Adhesive strips 21 for effecting the securement of the pad to the undergarment of the wearer is provided on the gauze surface that is adjacent to the impermeable plastic sheet 3. Such adhesive strips are generally covered with a sheet of paper 8 which can conveniently bear the trademark employed for the particular napkin. More importantly, the sheet of paper 8 overlies the entry slit 7b for the insertion of the transversely folded disposal bag 20.

Of course, to use the napkin, the paper sheet 8 is stripped off the adhesive on the backside of the gauze layer 7 and the pad is secured in position in the undergarment of the wearer. When the pad is soiled and disposal is desired, it is only necessary to pull the folded plastic bag 20 out of the slit 7b provided in the gauze material 7. To facilitate such removal, a paper tab 20a may be secured to the end of the folded plastic tube 20, but is not a requirement for the successful operation of this embodiment of the invention.

Although the invention has been described in terms of specified embodiments which are set forth in detail, it should be understood that this is by illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

I claim:

1. A sanitary napkin comprising an absorbent pad; a liquid impermeable sheet secured to one face of said pad; a perforated wrapper surrounding all portions of said pad and said impermeable sheet; said perforated wrapper having a slit-like opening extending transversely across one end of said napkin for a distance less than the full width of said napkin and disposed adjacent to said impermeable sheet; a flexible impermeable disposal bag dimensioned to receive said napkin within its interior without folding said napkin, said bag folded to an area substantially less than said impermeable sheet and insertable through said slit-like opening to lie between the outer face of said impermeable sheet and said perforated wrapper; and adhesive means on the outer face of that portion of said perforated wrapping adjacent said impermeable sheet for securing said assemblage to an undergarment.

2. The sanitary napkin of claim 1 further comprising a removable cover sheet overlying said adhesive means and said slit-like opening prior to usage of said napkin.

3. The sanitary napkin of claim 2 wherein said adhesive means comprises a plurality of bands of pressure sensitive adhesive and said removable cover sheet comprises paper.

4. The sanitary napkin of claim 1 wherein said perforated wrapper comprises gauze.

5. A sanitary napkin comprising an absorbent pad; a liquid impermeable sheet secured to one face of said pad; a flexible disposal bag having a height dimension approximately twice of width of said napkin and a length dimension approximately equal to said napkin, said bag folded to an area configuration substantially equal that of said liquid impermeable sheet; means for detachably retaining said disposal bag adjacent to the outer face of said liquid impermeable sheet; and means for securing all the aforementioned elements to an undergarment.

6. The sanitary napkin of claim 5 wherein said securing means comprises a band of contact adhesive applied to the face of said folded bag that is non-adjacent to said liquid impermeable sheet.

7. The sanitary napkin defined in claim 5 wherein said means for detachably retaining said disposal bag comprises a wrapper of gauze surrounding said absorbent pad, said liquid impermeable sheet, and said folded bag.

8. The sanitary napkin of claim 7 wherein said securing means comprises a band of contact adhesive applied to the outer face of said gauze wrapper lying adjacent to said folded bag.

9. The method of manufacturing a sanitary napkin with an integral disposal bag comprising the steps of:
forming by conventional procedures a conventional sanitary napkin having an absorbent pad and a liquid impermeable pad backing sheet;
forming by conventional procedures a flexible liquid impermeable disposal bag having a height dimension approximately twice the width of said napkin to receive said sanitary napkin within its interior without folding said napkin;
folding said flexible disposal bag to a dimensional area less than the area of said backing sheet; and
detachably securing said flexible disposal bag adjacent to said outer face of said backing sheet.

10. The method of claim 9 further comprising the steps of encasing said absorbent pad and liquid impermeable backing sheet with a perforated gauze-like wrapping having a slit on its side adjacent to said backing sheet; and inserting said folded disposal bag through said slit to retain said disposal bag in assembly with said sanitary napkin during use of said napkin.

11. A sanitary napkin comprising an absorbent pad; a liquid impermeable sheet secured to one face of said pad; a gauze-like wrapper surrounding all portions of said pad and said liquid impermeable sheet; said gauze-like wrapper having a slit-like opening extending transversely across one end of said sanitary napkin for a distance less than full width of said sanitary napkin and disposed adjacent to said liquid impermeable sheet; a flexible impermeable disposal bag dimensioned to receive said sanitary napkin within its interior, said flexible impermeable disposal bag being folded in an elongated manner to an area substantially less than said liquid impermeable sheet and inserted through said slit-like opening to lie between an outer face of said liquid impermeable sheet and said gauze-like wrapper; adhesive means on an outer face of that portion of said gauze-like wrapper adjacent said liquid impermeable sheet for securing said sanitary napkin to an undergarment; and tab means secured to one end of said folded flexible impermeable disposal bag for longitudinally pulling said folded flexible impermeable disposal bag out through said slit-like opening for disposing of said sanitary napkin therein after use.

* * * * *